US010537500B2

(12) United States Patent
Kim et al.

(10) Patent No.: US 10,537,500 B2
(45) Date of Patent: Jan. 21, 2020

(54) COSMETIC INCLUDING URETHANE FOAM IMPREGNATED WITH COSMETIC COMPOSITION

(71) Applicant: AMOREPACIFIC CORPORATION, Seoul (KR)

(72) Inventors: Kyung Nam Kim, Yongin-si (KR); Jung Sun Choi, Yongin-si (KR); Min Kyung Shim, Yongin-si (KR); Kyung Ho Choi, Yongin-si (KR); Yeong Jin Choi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 14/034,650

(22) Filed: Sep. 24, 2013

(65) Prior Publication Data

US 2014/0023689 A1   Jan. 23, 2014

Related U.S. Application Data

(63) Continuation-in-part of application No. PCT/KR2012/002141, filed on Mar. 23, 2012.

(30) Foreign Application Priority Data

Mar. 24, 2011 (KR) .......................... 10-2011-0026466

(51) Int. Cl.
| | |
|---|---|
| *A61K 8/02* | (2006.01) |
| *A61K 8/87* | (2006.01) |
| *A61Q 1/00* | (2006.01) |
| *A61Q 1/02* | (2006.01) |
| *A61Q 1/04* | (2006.01) |
| *A61Q 1/06* | (2006.01) |
| *A61Q 1/08* | (2006.01) |
| *A61Q 1/10* | (2006.01) |
| *A61Q 17/04* | (2006.01) |
| *C08L 75/06* | (2006.01) |
| *C08L 75/08* | (2006.01) |
| *C08G 101/00* | (2006.01) |

(52) U.S. Cl.
CPC .......... *A61K 8/0216* (2013.01); *A61K 8/0208* (2013.01); *A61K 8/87* (2013.01); *A61Q 1/00* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 17/04* (2013.01); *C08L 75/06* (2013.01); *C08L 75/08* (2013.01); *C08G 2101/00* (2013.01)

(58) Field of Classification Search
CPC ...... A61K 8/0216; A61K 8/0208; A61K 8/87; A61Q 1/00; A61Q 1/04; A61Q 1/06; A61Q 1/08; A61Q 1/10; A61Q 1/02; A61Q 17/04; C08L 75/06; C08L 75/08; C08G 2101/00

See application file for complete search history.

(56) References Cited

U.S. PATENT DOCUMENTS

| | | | |
|---|---|---|---|
| 1,851,462 A | 10/1932 | Steller | |
| 2,764,565 A | 9/1956 | Hoppe et al. | |
| 3,133,309 A | 5/1964 | Miles | |
| 3,463,745 A | 8/1969 | Hofrichter et al. | |
| 3,465,759 A | 9/1969 | Haefele | |
| 3,748,288 A | 7/1973 | Winkler et al. | |
| 4,130,121 A | 12/1978 | Wetzel | |
| 4,259,452 A | 3/1981 | Yukuta et al. | |
| 4,309,509 A | 1/1982 | Wood | |
| 4,323,656 A | 4/1982 | Strickman et al. | |
| 4,344,930 A | 8/1982 | MacRae et al. | |
| 4,374,935 A | 2/1983 | Decker et al. | |
| 4,427,798 A | 1/1984 | Konig et al. | |
| 4,440,181 A | 4/1984 | Scherer | |
| 4,537,912 A | 8/1985 | Griswold | |
| 4,594,835 A | 6/1986 | Gray | |
| 4,656,196 A | 4/1987 | Kelly et al. | |
| 4,706,693 A | 11/1987 | Spector | |
| 4,806,572 A | 2/1989 | Kellett | |
| 4,985,467 A | 1/1991 | Kelly et al. | |
| 5,064,653 A | 11/1991 | Sessions et al. | |
| 5,065,752 A | 11/1991 | Sessions et al. | |
| 5,098,621 A | 3/1992 | Hermann | |
| 5,296,518 A | 3/1994 | Grasel et al. | |
| 5,552,449 A | 9/1996 | Sollers et al. | |
| 5,591,779 A | 1/1997 | Bleys et al. | |
| 5,961,961 A | 10/1999 | Dobkowski et al. | |
| 6,271,277 B1 | 8/2001 | Bleys et al. | |
| 6,391,233 B1 | 5/2002 | Otani et al. | |
| 6,638,986 B2 | 10/2003 | Falke et al. | |
| 6,706,775 B2 | 3/2004 | Hermann et al. | |
| 7,427,412 B1 | 9/2008 | Painter et al. | |
| 7,612,160 B2 | 11/2009 | Nguyen-Kim et al. | |
| 8,784,854 B2 * | 7/2014 | Choi et al. ..................... | 424/401 |
| 9,532,637 B2 | 1/2017 | Choi et al. | |
| 2002/0182245 A1 | 12/2002 | Thomson | |
| 2004/0170670 A1 | 9/2004 | Smith et al. | |
| 2005/0159500 A1 | 7/2005 | Dreier et al. | |
| 2006/0235100 A1 | 10/2006 | Kaushiva et al. | |
| 2007/0189975 A1 | 8/2007 | Thomson | |
| 2009/0047495 A1 * | 2/2009 | Hubbs ............................ | 428/220 |
| 2011/0014254 A1 * | 1/2011 | Choi et al. ..................... | 424/401 |
| 2014/0023689 A1 | 1/2014 | Kim et al. | |
| 2015/0196468 A1 | 7/2015 | Kim et al. | |

FOREIGN PATENT DOCUMENTS

| | | |
|---|---|---|
| BE | 875638 | 8/1979 |
| DE | 2356460 | 5/1974 |

(Continued)

OTHER PUBLICATIONS

Notice of Allowance with English Translation for Application No. 10-2011-0026466 dated Apr. 17, 2013.

(Continued)

*Primary Examiner* — Hasan S Ahmed
(74) *Attorney, Agent, or Firm* — Rothwell, Figg, Ernst & Manbeck, P.C.

(57) ABSTRACT

Disclosed is a cosmetic including polyether-based urethane foam impregnated with a cosmetic composition. The cosmetic provides improved feeling in use, portability and stability.

15 Claims, 11 Drawing Sheets

(56) References Cited

FOREIGN PATENT DOCUMENTS

| | | |
|---|---|---|
| EP | 0528705 | 9/2000 |
| GB | 1498363 | 1/1978 |
| JP | 08325125 A | 12/1996 |
| JP | 3015878 B2 | 3/2000 |
| JP | 2002-53640 A | 2/2002 |
| JP | 2003012457 A | 1/2003 |
| JP | 2004267277 A | 9/2004 |
| JP | 2005-152186 A | 6/2005 |
| JP | 2006241150 A | 9/2006 |
| JP | 2007330771 A | 12/2007 |
| JP | 2010-6294 A | 1/2010 |
| JP | 4588357 B2 | 12/2010 |
| KR | 0131075 | 11/1997 |
| KR | 10-0498655 B1 | 7/2005 |
| KR | 1020090100643 A | 9/2009 |
| KR | 10-2013-0116044 A | 10/2013 |
| KR | 10-2014-0038880 A | 3/2014 |
| KR | 10-2015-0063196 A | 6/2015 |
| WO | 9947127 A1 | 9/1999 |
| WO | 2008112139 | 9/2008 |
| WO | 2009/116817 A2 | 9/2009 |
| WO | 2012/128589 A2 | 9/2012 |

OTHER PUBLICATIONS

Korean Office Action with English Translation for Application No. 10-2011-0026466 dated Dec. 16, 2012.
Korean Office Action with English Translation for Application No. 10-2011-0026466 dated Jun. 6, 2012.
International Search Report for International Application No. PCT/KR2012/002141 dated Oct. 31, 2012.
Written Opinion for International Application No. PCT/KR2012/002141 dated Oct. 31, 2012.
European Search Report—EP Application No. 12759918.1 dated Jan. 22, 2014 from European Patent Office.
George Woods, "Flexible Polyurethane Foams", Chemistry and Technology, 1982, pp. 94-95, Applied Science Publishers Ltd., Essex, England.
"Trend of Global Urethane Raw Materials and Products Market", KIET Overseas Industrial Information, Retrieved from the Internet Nov. 15, 2016, pp. 1-2, <URL: http://www.kiet.go.kr/servlet/isearch?mode=view&dataNo=43619>.
Polyurethane Foam, p. 1, <URL: http://web.archive.org/web/20090220164156/http://casefoam.com/Polyurethane-foam.htm>.
"Reticulated Polyurethane Foam: Quenching vs. Zapping", UFP Technologies, Retrieved from the Internet May 12, 2016, <URL: http://www.ufpt.com/resource-center/quenching-vs-zappingreticulated-polyurethane/>.
"Nature Republic CC Cushion Pact Sponge Gets Melted!!", Posted on the Internet Feb. 5, 2015, <URL: http://blog.haver.com/clawsome/220263606984>.
"BB Cushion Sponge is Melting", Posted on the Internet Feb. 4, 2015, <URL: http://www.todayhumor.co.kr/board/view.php?table=fashion&no=142195>.
"Reticulated Polyurethane Foam", UFP Technologies, Retrieved from the Internet Jul. 8, 2016, pp. 1-3, <URL: http://www.ufpt.com/materials/foam/reticulatedpolyurethane-foam.html>.
"Reticulated Open Cell Black Packaging Foam with Polyester Polyurethaner Material", Changzhou Dayetengfei Sponge Factory, Retrieved from the Internet Jul. 8, 2016, pp. 1-3, <URL: http://www.customizedfoam.com/sale-7566632-reticulatedopen-cellblack-packaging-foam-with-polyesterpolyurethaner-material.html>.
"Reticulated Foam-Polyurethane-based foam with open cellular structure", Material Sample Shop.com, Retrieved from the Internet Jul. 8, 2016, pp. 1-2, <URL: https://www.materialsampleshop.com/products/reticulatedfoampolyurethane-based-foam-with-open-cellular-structure>.
"Reticulated Foam" and "Open Cell Polyurethane Foam", Foam Engineers Limited, Retrieved from the Internet Jul. 8, 2016, pp. 1-2, <URL: http://www.foamengineers.co.uk/foammanufacturingsuppliers/reticulated-foam>.

Jong-Rae Park, "Catalytic Glycolysis of Polyether Urethane Foam Waste", Master's Thesis, Chonnam National University Graduate School, Department of Chemical Engineering, Aug. 1999, pp. 4-5, KR.
"Optimization Technology Support for Polyurethane Foam Production through Analysis of Correlations Between Cell Structure and Properties", Ministry of Commerce, Industry and Energy, Sep. 30, 2003, pp. 8, 11 and 12, KR.
Chang-Seop Oh, "Recent Prospect of Polyurethanes", ReSEAT Analysis Report, Sep. 10, 2004, pp. 1-7, KR.
"Reticulated Polyurethane Foam", FXI Innovations, Retrieved from the Internet Nov. 11, 2016, pp. 1-3, <URL: http://fxi.com/foamtechnologies/processes/reticulation.php>.
Polyurethane Foam, Retrieved from the Internet Nov. 15, 2016, pp. 1-2, <URL: https://web.archive.org/web/20021223120233/http://www.casefoam.com/Polyurethanefoam.htm>.
Reticulated Polyurethane Foam, UFP Techonologies, Retrieved from the Internet Jul. 8, 2016, pp. 1-3.
Reticulated Foam, Australian Foam Manufacturer, Joyce Foam Products, Retrieved from the Internet Nov. 10, 2016, <URL: http://www.joyce.com.au/foams/reticulatedfoam/>.
"Filters for Fishkeeping", EMW filtertechnik, Product Brochure, Retrieved from the Internet Nov. 22, 2016, pp. 1-4, <URL: www.emw.de>.
Open Cell Foam, The Foam Factory, Retrieved from the Internet Nov. 11, 2016, pp. 1-2, <URL: http://www.thefoamfactory.com/opencellfoam/filter.html>.
"Reticulated (Open-Cell) & Non-Reticulated (Closed-Cell) Foam Swabs", Berkshire, Retrieved from the Internet Nov. 11, 2016, pp. 1-5, <URL: http://www.berkshire.com/shop/cleanroomcleaningswabs/foam.html>.
"100% Open Cell Flexible Polyurethane Foams", FXI Reticulated Foams, Product Sheet, FXI, Inc., Retrieved from the Internet Nov. 22, 2016, 1 page, <URL: fxi.com>.
Seong-Mi Park, Researcher's Statement, COSMAX R&I Institute, Apr. 17, 2017, 1 page.
Test Result Sheet, Stability Test of LLBB Cushion, Korea Conformity Laboratories, 2017, pp. 1-5.
Seong-Mi Park, "Report on Stability Test of Sponge Impregnated with LLBB Cushion Cosmetic Composition", Cosmax R&I Institute, Apr. 19, 2017, pp. 1-5, Korea.
Sang-Beom Kim, "About Structure and Properties of Polyurethane Foam", Letter of Opinion, May 9, 2016, pp. 1-4.
European Office Action for corresponding European Patent Application No. 12759918.1 dated Mar. 1, 2016.
Canadian Office Action for corresponding Canadian Patent Application No. 2,804,298 dated Jan. 4, 2016, citing U.S. Pat. No. 3,133,309 and previously filed references.
Canadian Office Action for corresponding Canadian Patent Application No. 2,804,298 dated Sep. 12, 2016.
Canadian Office Action for corresponding Canadian Patent Application No. 2,804,298 dated Jan. 18, 2017, citing previously filed reference.
Chinese Office Action for corresponding Chinese Patent Application No. 201280002267.3 dated Mar. 30, 2016.
Chinese Patent Invalidation Request for corresponding Chinese Patent Application No. 201280002267.3.
Japanese Office Action for corresponding Japanese Patent Application No. 2014-008657 dated May 31, 2016, citing previously filed reference.
Japanese Office Action for corresponding Japanese Patent Application No. 2014-008657 dated Mar. 9, 2017, citing previously filed reference.
Indian Office Action—Indian Application No. 10805/CHENP/2012 dated Jul. 14, 2017, citing references listed within.
Extract from pp. 22-23 of Korean Patent Court Ruling (case No. 2016heo8667), 1 page.
Foaming Plant, Copyrights 2006, pp. 1-7, Retrieved from the Internet Jun. 25, 2018<URL:http://www.foamtecintl.com/index.php?shpage=vpage&vpage=fpprofile&lang=en&plan=FP>.
Tony Abisaleh et al., "Polyurethane Technology & Applications", 18 pages.

(56) References Cited

OTHER PUBLICATIONS

Result report of reproduction experiments on Amorepacific's patent (No. 1257628), 2017, 21 pages.
Reticulated foam, Edited on Jun. 3, 2018, pp. 1-3, Retrieved from the Internet Jun. 15, 2018<URL:https://en.wikipedia.org/wiki/Reticulated_foam>.
Notice of Opposition for EP 12759918.1 from European Patent Office dated Jul. 19, 2018, citing the above references.
Canadian Office Action—Canadia Application No. 2804298 dated May 29, 2014.
Canadian Office Action—Canadia Application No. 2804298 dated Oct. 28, 2013.
Canadian Office Action—Canadian Application No. 2804298 dated May 6, 2015, citing U.S. Pat. No. 3,133,309.
Canadian Protest—Canadia Application No. 2804298 dated Mar. 30, 2015, citing U.S. Pat. No. 3,133,309.
Chinese Office Action—Chinese Application No. 201280002267.3 dated Dec. 3, 2014, citing previously filed references CN101977587 and JP4588357.
Chinese Office Action—Chinese Application No. 201280002267.3 dated Mar. 18, 2014, citing previously filed references CN101977587 and US20090047495.
Chinese Office Action—Chinese Application No. 201280002267.3 dated Sep. 8, 2015.
European Office Action—European Application No. 12759918.1 dated Aug. 11, 2015.
European Office Action—European Application No. 12759918.1 dated Jun. 18, 2015, citing U.S. Pat. No. 3,133,309.
European Office Action—European Application No. 12759918.1 dated Oct. 12, 2014, citing previous filed references.
INOAC—Reticulated PU FOAM, Posted: Nov. 2009, p. 1, Retrieved from the Internet Sep. 2, 2015, <URL: http://www.inostech.com/>.
Japanes Office Action-Japan Application No. 2014-008657 dated Jun. 18, 2015, citing previous filed references.
Japanese Office Action—Japan Application No. 2014-008657 dated Sep. 11, 2015, citing previous filed references.
Malaysian Examination Report—Application No. PI2013000328 dated Apr. 3, 2015, citing previous filed references.
Shimin Wu, et al., "Concise Dictionary of Fine Chemicals", Shenyang: Liaoning Science and Technology, (Jun. 1999), pp. 1-7.
Singaporean Written Opinion—Application No. 201209361-3 dated Sep. 9, 2013, citing previouse filed refrerences.
Taiwanese Office Action—TW Application No. 101109975 dated Feb. 10, 2014, citing previous filed references.
Taiwanese Office Action—TW Application No. 101109975 dated Jan. 13, 2014, citing previous filed references.
UFP Technologies—Reticulated Foam, (Copyright 2011), pp. 1-2, Retrieved from the Internet Sep. 2, 2015, <URL: http://www.ufpt.com/>.
Decision of Intellectual Property Trial and Appeal Board, 6th Department, Trial No. 2018Dang (decision reversing the original decision)76.
Decision of Intellectual Property Trial and Appeal Board, 7th Department, Trial No. 2018Jeong49.
Decision of Patent Court, 1st Dvision, Case No. 2016Heo8667 Invalidation of Registration (Patent).
Decision of Supreme Court, 1st Division, Case No. 2018Hu10596 Invalidation of Registration (Patent).
Kamicokrolock, "Review, Etude house Cushion Foundation", website contents, Mar. 14, 2015, 3 pages.
Merquinsa, Polyurethane Types, Web site contents, pp. 1-8.
Meyer R. Rosen (ed.), Delivery System Handbook for Personal Care and Cosmetic Products, 2005, pp. 513-525.
Michael Szycher, Szycher's Handbook of Polyurethanes, 1999, p. 7-6.
Michael Szycher, Szycher's Handbook of Polyurethanes, 1999, pp. C-8, 21, and 24.
Mihail Ionescu, "Chemistry and Technology of Polyols for Polyurethanes", 2005, pp. 2-4, 49-50, 263, 538-540, 547, Rapra Technology Limited.
Polyurethane Technology & Applications, pp. 107-108.
Polyurethane Technology & Applications, pp. 311-330.
Polyurethane Technology & Applications, pp. 3-5, 89-90, 123, 125, 169-171, 223-226.
T. Thomson, Design and Applications of Hydrophilic Polyurethanes, 2000, pp. 1-9, Preface xi-xiii.
www.ifacemaker.com, a review on Almay Nearly Naked Foundation, May 29, 2003.
Alain Parfondry, "Polyurethane Technology & Applications", 15 pages, Nov. 2002.
Declaration of R. Randall Wickett, Petition for Inter Partes Review of U.S. Pat. No. 8,784,854 under U.S.C. §§311-319 and 37 C.F.R. §§42.1-.8, 42.100-, 123, Jul. 27, 2018, 90 pages.
The HLB System, a time-saving guide to emulsifier selection, 22 pages, Mar. 1980.
Declaration of Robert Y. Lochhead, Ph.D., FRSC, Case IPR2018-01516, U.S. Pat. No. 8,784,854 B2, dated Nov. 30, 2018, 185 pages.
Petition for Inter Partes Review of U.S. Pat. No. 8,784,854 under U.S.C. §§311-319 and 37 C.F.R. §§42.1-.8, 42.100-.123, dated Aug. 6, 2018, 78 pages.
Patent Owner's Preliminary Response, Case IPR2018-01516, U.S. Pat. No. 8,784,854 B2, dated Nov. 30, 2018, 70 pages.
Decision: Denying Institution of Inter Partes Review 35 U.S.C. § 314(a), Case IPR2018-01516, U.S. Pat. No. 8,784,854 B2, Feb. 20, 2019, 29 pages.

\* cited by examiner

COSMETIC INCLUDING URETHANE FOAM IMPREGNATED WITH COSMETIC COMPOSITION

BACKGROUND

1. Field

The present disclosure relates to a cosmetic including urethane foam.

2. Description of the Related Art

Polyester-based urethane foam tends to be brittle under wet environment and has a small cell structure and low air permeability. Thus, polyester-based urethane foam shows low cushioning property, softness and flexibility, so that it is not suitable for impregnation with a cosmetic composition, particularly a liquid cosmetic composition. Therefore, there has been a need for developing urethane foam suitable for impregnation with a cosmetic composition.

SUMMARY

The present disclosure is directed to providing cosmetic composition-impregnated urethane foam, which maintains high stability of the cosmetic composition.

In one aspect, there is provided cosmetic composition-impregnated polyether-based urethane foam.

In another aspect, there is provided a cosmetic including polyether-based urethane foam impregnated with a cosmetic composition.

The polyether-based urethane foam disclosed herein maintains high stability even after it is impregnated with a cosmetic composition, shows high durability and excellent filling ability and dischargeability when it is impregnated with a cosmetic composition, and thus is suitable for impregnation with a cosmetic composition. The polyether-based urethane foam disclosed herein enhances the portability and feeling in use of a cosmetic composition.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
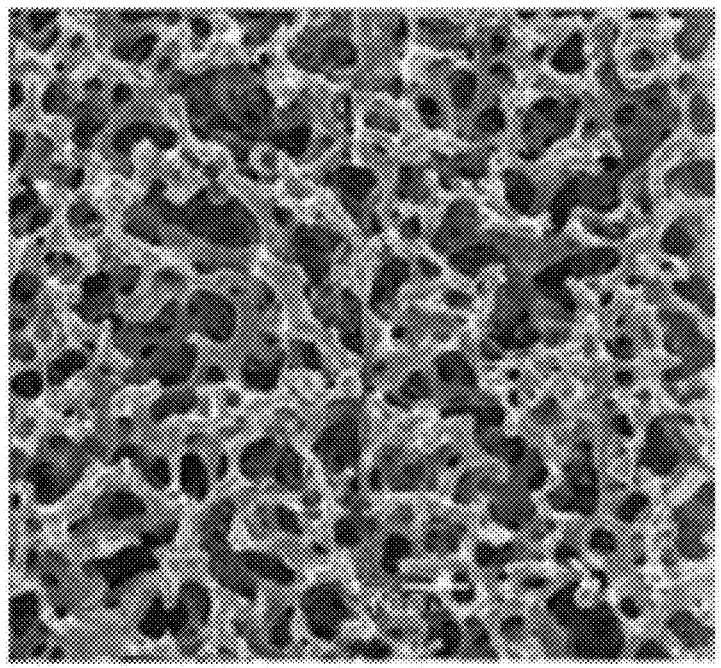
FIG. 1 is an optical microscopic image (NIKON ECLIPSE 80i) of polyether-based urethane foam.

Exemplary embodiments now will be described more fully hereinafter with reference to the accompanying drawings, in which exemplary embodiments are shown.

In one aspect, there is provided cosmetic composition-impregnated polyether-based urethane foam. In another aspect, the polyether-based urethane foam may function as a carrier on which a cosmetic composition is supported and retained.

As used herein, "urethane foam" means a foamed and solidified polyurethane resin, and may also be expressed as "foamed urethane".

As used herein, "durability" means a degree of any material to maintain as it is without melting, tearing or swelling when the material is impregnated with a cosmetic composition and stored at a predetermined temperature for a predetermined time. As used herein, "filling ability" means ability of any material to fill a cosmetic composition therein, and may be represented as time required for filling a predetermined amount of cosmetic composition. As used herein, "dischargeability" means an amount of cosmetic composition discharged when taking the cosmetic composition from any material impregnated therewith. When taking the cosmetic composition, the cosmetic composition is required to be discharged in an adequate amount, not too much, but not too little.

According to an embodiment, the urethane foam, particularly polyether-based urethane foam disclosed herein maintains high durability even after it is impregnated with a cosmetic composition, allows easy filling of a cosmetic composition, an discharges an adequate amount of cosmetic composition, as compared to other materials, including acrylonitrile-butadiene rubber (NBR), styrene-butadiene rubber (SBR), natural rubber (NR), PU-PE flocking, polyethylene (PE), ethylene vinyl acetate (EVA), polyolefin (PO) and polyvinyl alcohol (PVA). Thus, the urethane foam disclosed herein is suitable for impregnation with a cosmetic composition.

According to another embodiment, urethane foam, particularly polyether-based urethane foam is more resistant against humidity as compared to polyester-based urethane foam, and thus shows low brittleness and high stability even under a high-humidity condition. Particularly, polyether-based urethane foam shows higher durability after being impregnated with a cosmetic composition, as compared to polyester-based urethane foam, and thus is suitable for impregnation with a cosmetic composition. In addition, polyether-based urethane foam has a larger cell structure as compared to polyester-based urethane foam, and thus shows higher air permeability, cushioning property, softness and flexibility. Further, polyether-based urethane foam has higher cost efficiency as compared to polyester-based urethane foam.

According to still another embodiment, the polyether-based urethane foam is impregnated with cosmetic composition, which is different as compared to a conventional cosmetic applicator (puff or cosmetic sponge). The cosmetic applicator is used when a user applies a cosmetic composition on a skin. Specifically, it is used when a cosmetic is applied to a skin in such a way to touch an applicator with a cosmetic composition on a skin. The cosmetic applicator itself does not contain any cosmetic composition, whereas the impregnation material for cosmetic composition impregnates and stores a cosmetic composition before a user actually uses it (durability and filling property are necessary). When the user actually uses it, a proper amount of cosmetic composition is applied to a cosmetic applicator (discharging property is necessary). The impregnation material for a cosmetic composition of the present invention does not directly contact with a skin, but contains a cosmetic composition, so a certain applicator is necessary. In case of a cosmetic applicator, specifically, a puff, when a cosmetic composition penetrates deep into the inner side of a sponge, the cosmetic composition is not easy to be applied to a user's skin when in use, so the cosmetics should not easily penetrate into the deep portion of the sponge. The cosmetic composition-impregnated foam according to the present invention itself is an impregnation material of a cosmetic composition which has an impregnation function, so it is definitely different from a cosmetic applicator (puff).

Figure 6:
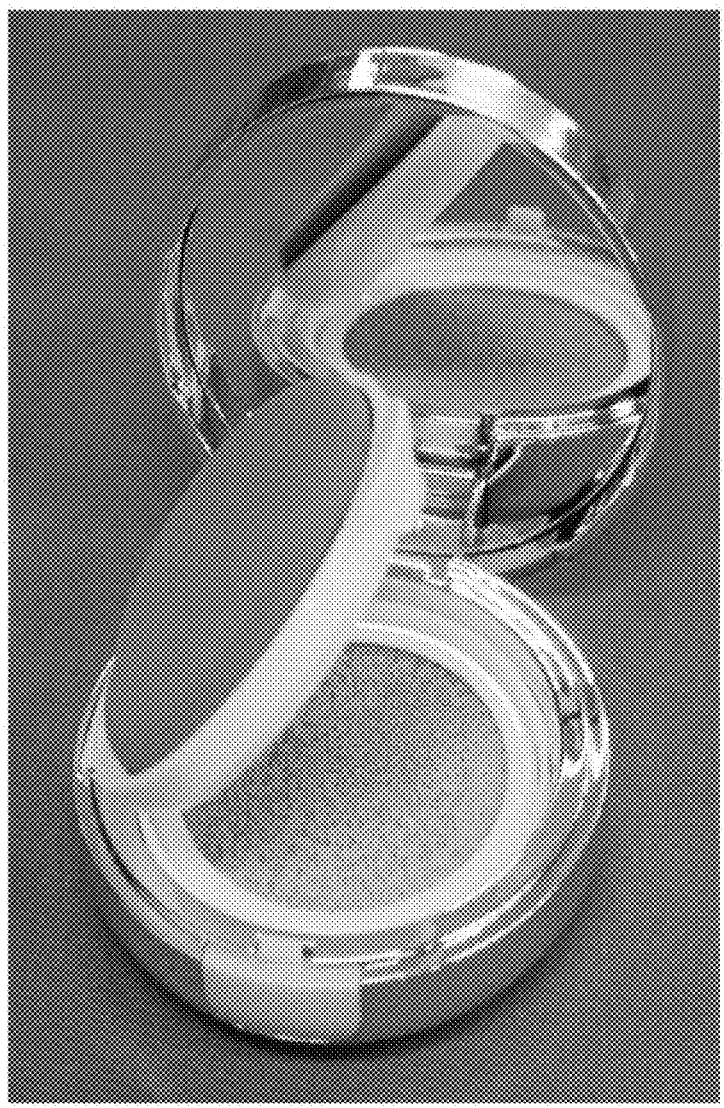
FIG. 6 shows a pact with a built-in urethane foam impregnated with a W/O type emulsified make-up cosmetic composition.

FIG. 6 is a view illustrating a product containing an impregnation material for a cosmetic composition with which a cosmetic composition of the present invention is impregnated.

According to still another embodiment, urethane form may have a reticulated structure. In the case of a reticulated structure, it is easy to carry out homogeneous impregnation of urethane foam with a cosmetic composition, thereby providing a higher impregnation ratio.

Figure 7:
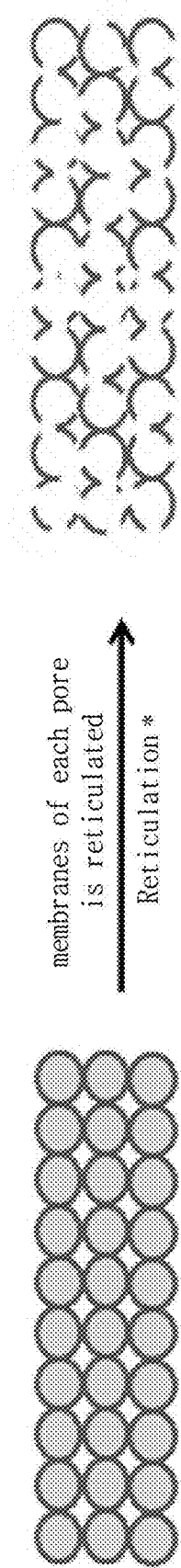
FIG. 7 is a 3D view illustrating a reticulated structure of a polyether-based urethane foam.

The reticulated structure urethane foam according to the present invention is formed by an additional process. The reticulated structure is also called a 3D network structure. The reticulated structure is made in a network shape as the balloon-shaped membranes (walls) are reticulated. The reticulated structure has features in that air can penetrate, and liquid can be absorbed and discharged. The "reticulation" is a kind of process for changing to a reticulated structure depending on its application after a foamed structure is made. In case of a sponge foam, the membranes of each pore is broken and reticulated. The reticulation process is shown in FIG. 7. The reticulated structure of the present invention is different from a conventional foamed structure in which cosmetic composition cannot penetrate deep into the inner side having a 3D membrane structure in a sponge. The present invention is also different from the top of the urethane foam support covered by cloth, net, non-woven fabric, etc.

According to still another embodiment, urethane foam may have an open cell structure.

The urethane foam made through a foaming and concreting process has a closed cell or semi-open cell structure. When urethane foam has a closed cell structure, air bubbles may be trapped in urethane so that the urethane foam may not be impregnated with a low-viscosity emulsified cosmetic composition easily. The present invention can provide a complete open cell structure in which only frames remain after the cell surfaces of the foams are reticulated through the reticulation process.

According to still another embodiment, urethane foam may have a density of 1-3 pcf (pounds per cubic feet), particularly 1-2 pcf. When urethane foam has a density less than 1 pcf, an excessively large amount of cosmetic composition may be discharged, thereby interrupting comfort in use. On the other hand, when urethane foam has a density more than 3 pcf, pores in which a cosmetic composition may be impregnated are insufficient so that the cosmetic composition may not be impregnated effectively.

Herein, density may be determined, for example, based on ASTM D3547.

According to still another embodiment, urethane foam may have a pore number of 70-120 ppi (pore per inch, number of pores per inch), particularly 75-95 ppi. When urethane foam has a pore number less than 70 ppi, it shows low elasticity, provides no comfort in use, and has difficulty in controlling the flowability of a cosmetic composition. When urethane foam has a pore number larger than 120 ppi, it shows low durability and provides an unsatisfactory feeling in use of the impregnated cosmetic composition.

As used herein, 'ppi' (pore per inch) is a unit expressing the size of a pore, and refers to the number of pores per inch, i.e., pore number shown on a 1-inch line in the section of a foam material. As a ppi number increases, pore size decreases. Since such a pore number is determined by visual inspection, recognition of pores depends on condition of pores, approved in different manners by different countries. For example, Visual Counting Methods (ppi check) of Japan, USA and Europe are shown in the following Table 1.

TABLE 1

| Visual Counting Methods (ppi check) | | | |
| --- | --- | --- | --- |
| Determination of ppi | Japan | USA | Europe |
| Method | Count only full cells (completely shaped cells) corresponding to the designated line as observed by a microscope | Count full cells (completely shaped cells within the designated line and on the boundary) observed by a microscope; 1.8 times of the value determined in Japan | Count all cells (all cells observed within the designated line and on the boundary, regardless of cell shapes) observed by a microscope; 2 times of the value determined in Japan |

Herein, Visual Counting Method of USA is used to determine ppi. Therefore, the ppi of urethane foam according to an aspect is different by about 30 ppi from the ppi thereof determined by using Visual Counting Method of Japan.

The cell size of the present invention is an average value measured using an optical microscope (NIKON ECLIPSE 80i).

According to still another embodiment, urethane foam before a cosmetic composition is impregnated may have an ASKER hardness of 10-70, particularly 20-60, and more particularly 35-55, as measured by a durometer (DUROMETER HARDNESS METER F Type, manufactured by ASKER). When urethane foam has a hardness less than 10 and is too soft, the cosmetic composition supported on urethane foam may be discharged in an excessively large amount, when taking it with a cosmetic utensil, such as nitrile butadiene rubber (NBR) puff or by hand, for use in taking a cosmetic composition enclosed in a pact container. On the other hand, when urethane foam has a hardness larger than 70 and is too hard, it is difficult to discharge a cosmetic composition from the urethane foam.

According to still another embodiment, the cosmetic composition applicable to the urethane foam for impregnation may be a liquid cosmetic composition, particularly an emulsified cosmetic composition, and more particularly a water in oil (W/O) type or oil in water (O/W) type emulsified cosmetic composition.

According to still another embodiment, an emulsified cosmetic composition may have a low viscosity, particularly of 5,000-15,000 cps (centipoise), and more particularly of 6,000-10,000 cps. When an emulsified cosmetic composition has a viscosity less than 5,000 cps, oil phase/aqueous phase separation occurs right after preparing the emulsified cosmetic composition. As a result, it is difficult to impregnate urethane foam with such a composition. When an emulsified cosmetic composition has a viscosity higher than 15,000 cps, it provides an undesirable tacky and heavy touch feel during skin application.

According to still another embodiment, the viscosity may be determined by a viscometer. The measured values may include LVDV II+PRO or RVDV III ULTRA, spindle No. 63 or spindle No. 64, speed RPM or 12 RM, the values of which are not limited thereto. The viscosity value may vary with systems used for measurement, spindle number, rpm, or the like.

According to yet another embodiment, the cosmetic composition may include a cosmetic composition for skin care and a cosmetic composition for make-up. Particularly, the cosmetic composition may be formulated into make-up primer, make-up base, foundation, powder, twin cake, lipstick, lip gloss, eye shadow, eye brow, concealer, lip liner, blusher, UV protector, lotion, cream, or essence, and more particularly, make-up primer, make-up base, liquid or solid foundation, powder, twin cake, lipstick, lip gloss, eye shadow, eye brow, concealer or blusher, but is not limited thereto.

Figure 2:
FIG. 2 shows a pact having urethane foam impregnated with a W/O type emulsified make-up cosmetic composition therein.
Figure 3A:
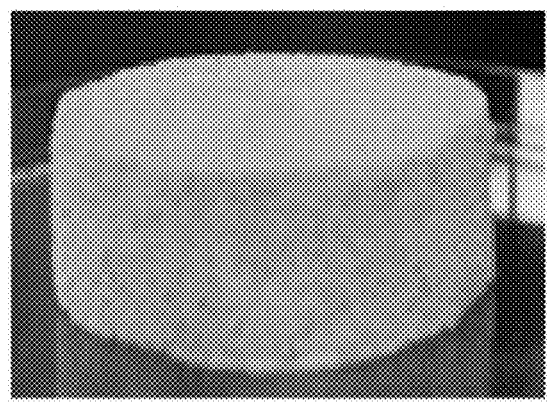
FIG. 3 shows ten types of materials each of which is impregnated with 15 g of a cosmetic composition and then stored at 55° C. for 7 days (a: NBR, b: SBR, c: NR, d: PU-ether, e: PU-ester, f: flocking, g: PE, h: EVA, i: PO, j: PVA)
Figure 3B:
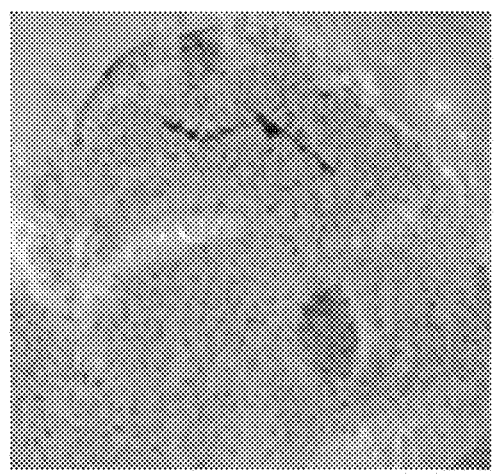
Figure 3C:
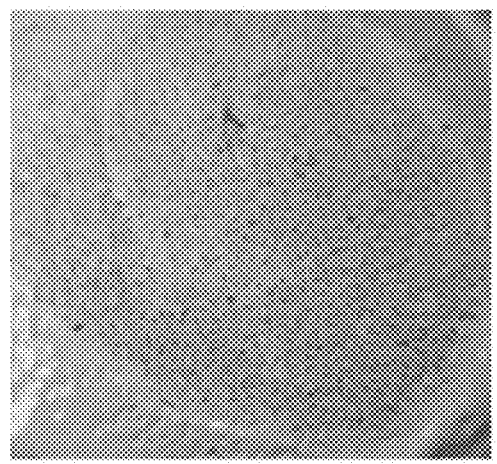
Figure 3D:
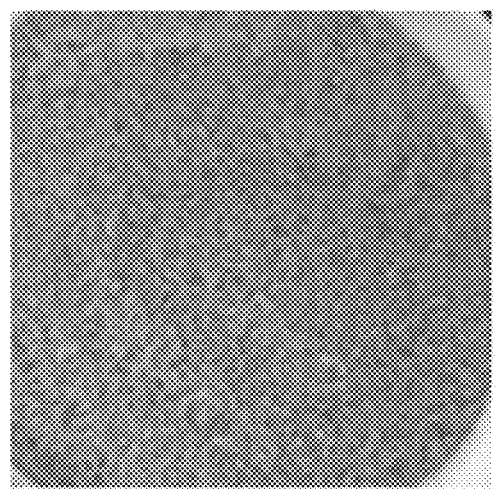
Figure 3E:
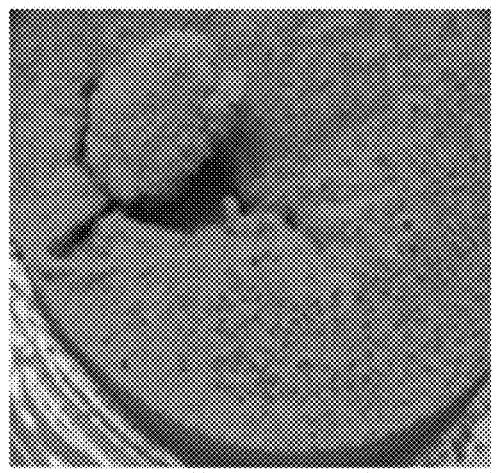
Figure 3F:
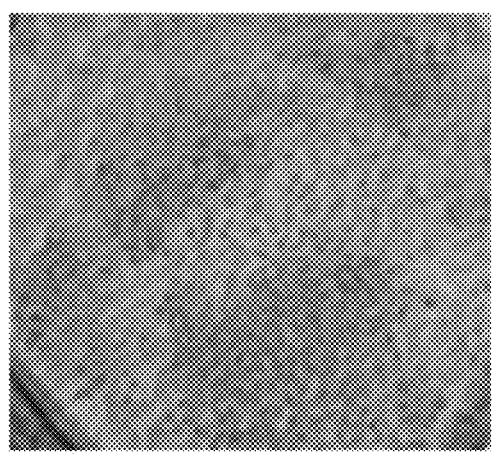
Figure 3G:
Figure 3H:
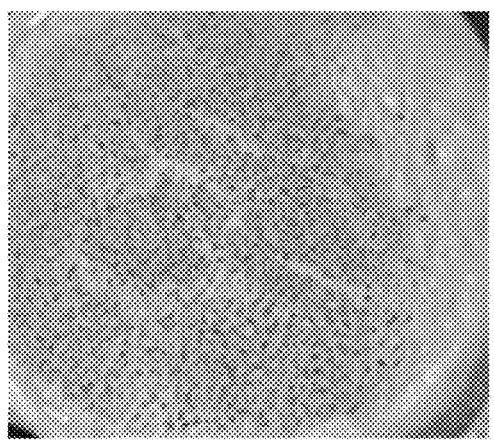
Figure 3I:
Figure 3J:
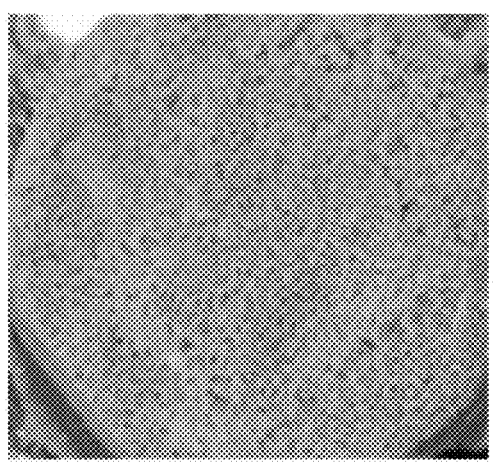

In another aspect, there is provided a cosmetic including the polyether-based urethane foam impregnated with a cosmetic composition. The cosmetic includes a cosmetic composition applied to the polyether-based urethane foam disclosed herein. Therefore, the cosmetic allows good packing of a cosmetic composition, supports a cosmetic composition homogeneously for a long time, enables an adequate amount of cosmetic composition to be discharged therefrom when taking the cosmetic composition, and maintains high durability and stability for a long time. In still another aspect, the cosmetic may be provided as a cosmetic container generally called 'pact' in brief and including a container that has a bottom portion in which the polyether-based urethane foam is received, and a top portion as a lid to which a mirror or the like may be attached. Such polyether-based urethane foam provided in a pact container is shown in FIG. 2.

The examples, comparative examples, preparation examples and test examples will now be described to describe the construction and effects of the present disclosure in more detail. The following examples, comparative examples, preparation examples and test examples are for illustrative purposes only and not intended to limit the scope of the present disclosure.

[Test Example 1] Investigation of Characteristics of Material

To select a material suitable for impregnation of a cosmetic composition, the following ten types of materials are provided: acrylonitrile-butadiene rubber (NBR), styrene-butadiene rubber (SBR), natural rubber (NR), polyether-based urethane (PU-ether), polyester-based urethane (PU-ester), PU-PE flocking (flocking), polyethylene (PE), ethylene vinyl acetate (EVA), polyolefin (PO) and polyvinyl alcohol (PVA). Each material has the characteristics as shown in the following Tables 2 and 3.

TABLE 2

|  | NBR | SBR | NR | PU-ether | PU-ester |
|---|---|---|---|---|---|
| Characteristics | Controllable pore size, elastic | Controllable pore size, soft and elastic | Controllable pore size, soft and elastic | Variable pore size | Variable pore size |
| Pore size | 70-100 ppi | 70-100 ppi | 70-100 ppi | 88-100 ppi | 88-100 ppi |

TABLE 3

|  | flocking | PE | EVA | PO | PVA |
|---|---|---|---|---|---|
| Characteristics | Used for cosmetic puff | Moisture-resistant, highly heat insulating | Light and soft | Open cell structure, soft | Uniform and continuous open cell structure, excellent water-retaining, water-absorbing and dust-absorbing properties |
| Pore size | 70-90 ppi | 80-100 ppi | 80-100 ppi | 90-110 ppi | 70-100 ppi |

[Test Example 2] Evaluation of Durability

The ten types of materials as described in Test Example 1 are selected and classified into two groups having a similar pore size, and are evaluated for durability. The test method will be described in detail hereinafter.

Each material is formed into a circular shape having a size of diameter 48 mm×thickness 10 mm, and is impregnated with 15 g of the same cosmetic composition having a viscosity of 10,000 cps. Then, each material is stored at 55° C. for 7 days and checked for its condition. The results are shown in the following Tables 4 and 5.

TABLE 4

| NBR | SBR | NR | PU-ether | PU-ester |
|---|---|---|---|---|
| Inappropriate, swelled with cosmetic composition | Easily torn when pressed with finger | Easily torn when pressed with finger | Appropriate, maintaining shape and volume | Melted, cracked when pressed with finger |

TABLE 5

| flocking | PE | EVA | PO | PVA |
|---|---|---|---|---|
| Melted, stuck on bottom of container | Good, maintaining shape and volume | Good, maintaining shape and volume | Melted, stuck on bottom of container | Good, maintaining shape and volume |

FIG. 3 shows each of the materials after it is impregnated with a cosmetic composition and stored for 7 days (a: NBR, b: SBR, c: NR, d: PU-ether, e: PU-ester, f: flocking, g: PE, h: EVA, i: PO, j: PVA).

As can be seen from FIG. 3, polyether-based urethane foam maintains its shape and volume even after being impregnated with a cosmetic composition, and thus shows the highest durability.

[Test Example 3] Evaluation of Filling Ability

Figure 4:
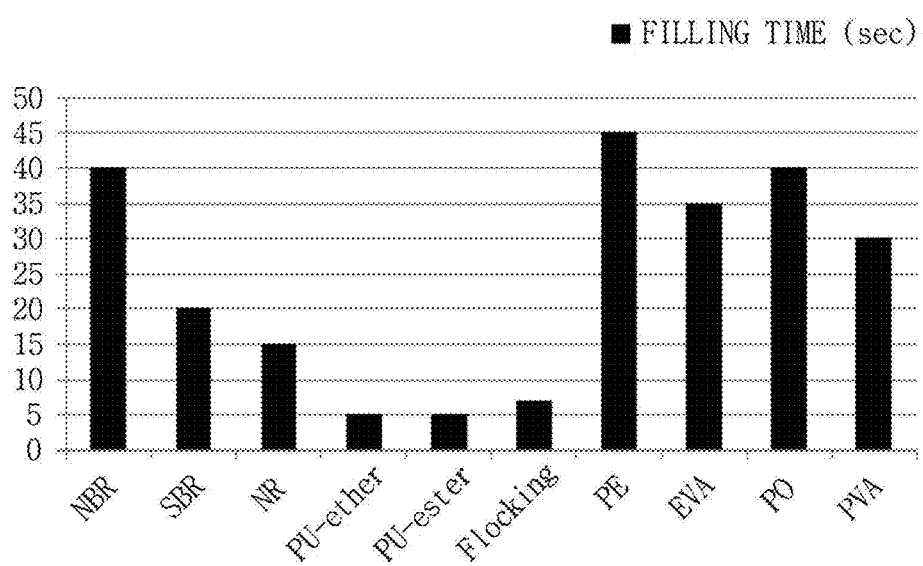
FIG. 4 is a graph illustrating the time required for impregnation of 15 g of the same cosmetic composition in each of the ten types of materials.

The ten types of materials as described in Test Example 1 are selected and classified into two groups having a similar pore size, and are evaluated for filling ability. Particularly, each material is formed into a circular shape having a size of diameter 48 mm×thickness 10 mm. Then, measured is the time required for each material to be impregnated with 15 g of the same cosmetic composition having a viscosity of 10,000 cps. The results are shown in the following Table 6 and FIG. 4.

TABLE 6

|  | Filling time (sec) |
|---|---|
| NBR | 40 |
| SBR | 20 |
| NR | 15 |
| PU-ether | 5 |
| PU-ester | 5 |
| flocking | 7 |
| PE | 45 |
| EVA | 35 |
| PO | 40 |
| PVA | 30 |

As can be seen from the above results, polyether-based urethane foam and polyester-based urethane foam have the smallest filling time. This suggests that polyether-based urethane foam and polyester-based urethane foam have the highest cosmetic composition filling ability.

[Test Example 4] Evaluation of Dischargeability (1) Investigation of Optimum Discharge Amount First, to investigate the amount of a cosmetic composition suitable as a unit discharge amount, 50 persons are allowed to apply different amounts of cosmetic composition and to evaluate each of the following items from which the optimum amount may be derived by rating it as grade 1 to grade 9 (higher grade represents better quality). The results are shown in the following Table 7. "Applicability" refers to a degree of goodness of skin application amount, "cosmetic effect" refers whether or not the cosmetic composition shows excellent coverage on skin without agglomeration and allows uniform make-up within an adequate time, "comfort" refers to a degree of comfort in use of cosmetic composition without take-up many times while allowing easy control of application amount, and 'satisfaction' refers to a degree of overall satisfaction.

TABLE 7

| Unit application amount (g) | Applicability | Cosmetic effect | Comfort | Satisfaction |
|---|---|---|---|---|
| 0.05 | 1 | 1 | 1 | 1 |
| 0.1 | 1 | 1 | 1 | 1 |
| 0.3 | 7 | 5 | 5 | 5 |
| 0.5 | 9 | 9 | 9 | 9 |
| 0.7 | 5 | 5 | 3 | 3 |
| 0.9 | 1 | 3 | 1 | 1 |
| 1.1 | 1 | 1 | 1 | 1 |
| 1.3 | 1 | 1 | 1 | 1 |
| 1.5 | 1 | 1 | 1 | 1 |

As can be seen from the above results, when the unit application amount of a cosmetic composition is 0.3-0.5 g, particularly is about 0.5 g, a high cosmetic effect, comfort and satisfaction are obtained. Therefore, it can be seen that when a cosmetic composition is taken once, 0.3-0.5 g, particularly about 0.5 g is adequate as a unit application amount.

(2) Evaluation of Dischargeability

Figure 5:
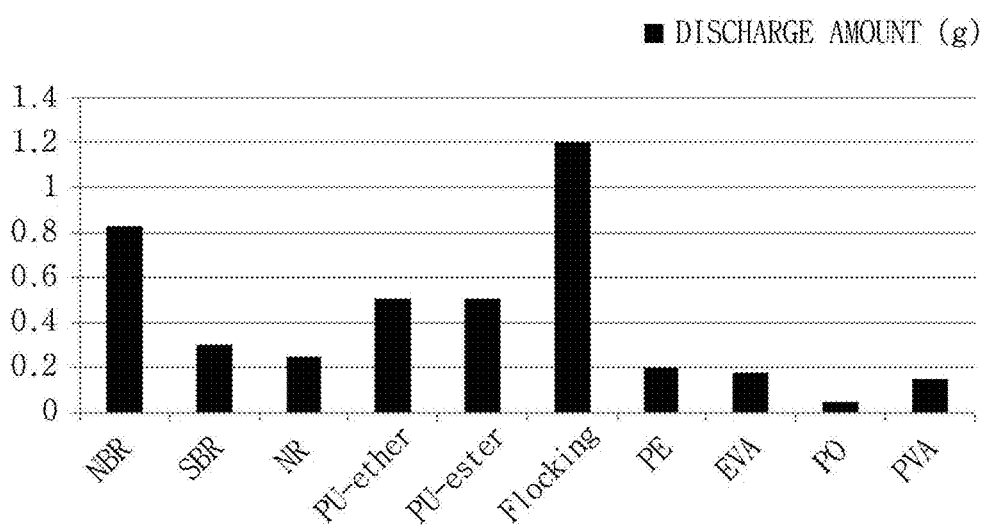
FIG. 5 is a graph illustrating the amount (g) of cosmetic composition discharged when taking the cosmetic composition from each of the ten types of materials impregnated with the same cosmetic composition.

The ten types of materials as described in Test Example 1 are selected and classified into two groups having a similar pore size, and are evaluated for dischargeability. Particularly, each material is impregnated with 15 g of the same cosmetic composition having a viscosity of 10,000 cps, and the amount (g) of cosmetic composition discharged when taking the cosmetic composition once by using puff. In addition, 50 persons are allowed to apply a cosmetic composition by using the ten types of materials, and to evaluate each of applicability, cosmetic effect, comfort and satisfaction by rating it as grade 1 to grade 9 (higher grade represents better quality). The results are shown in the following Table 8 and FIG. 5.

TABLE 8

|  | Discharge amount (g) | Applicability (grade) | Cosmetic effect (grade) | Comfort (grade) | Satisfaction (grade) |
|---|---|---|---|---|---|
| NBR | 0.83 | 1 | 3 | 1 | 1 |
| SBR | 0.3 | 5 | 7 | 5 | 5 |
| NR | 0.25 | 3 | 7 | 3 | 3 |
| PU-ether | 0.5 | 9 | 9 | 9 | 9 |
| PU-ester | 0.5 | 9 | 9 | 9 | 9 |
| Flocking | 1.2 | 1 | 1 | 1 | 9 |
| PE | 0.2 | 3 | 5 | 3 | 3 |
| EVA | 0.18 | 3 | 3 | 1 | 3 |
| PO | 0.05 | 1 | 1 | 1 | 1 |
| PVA | 0.15 | 1 | 1 | 1 | 1 |

As can be seen from the above results, polyether-based urethane foam and polyester-based urethane foam show the most adequate discharge amount. In addition, polyether-based urethane foam and polyester-based urethane foam provide excellent applicability, cosmetic effect, comfort and satisfaction. This means that polyether-based urethane foam and polyester-based urethane foam shows the highest cosmetic composition dischargeability.

As can be seen from the foregoing, polyether-based urethane foam having excellent durability, filling ability and dischargeability of a cosmetic composition is suitable for use in impregnation with a cosmetic composition.

What is claimed is:

1. A cosmetic product comprising:
   polyether-based urethane foam impregnated with a cosmetic composition, wherein the polyether-based urethane foam has a reticulated structure; and
   a container, in which the polyether-based urethane foam impregnated with the cosmetic composition is disposed,
   wherein the cosmetic composition is discharged from the polyether-based urethane foam to a cosmetic applicator, which is detached from the polyether-based urethane foam, and
   the density of the polyether-based urethane foam is 1-3 pcf (pounds per cubic feet) before the cosmetic composition is impregnated,
   wherein the polyether-based urethane foam has a pore number of 70-120 ppi (number of pores per inch) before the cosmetic composition is impregnated, and
   wherein the cosmetic composition is a water in oil (W/O) type or oil in water (O/W) type emulsified cosmetic composition.

2. The cosmetic product according to claim 1, wherein the polyether-based urethane foam has a hardness of 10-70 being measured with a durometer before the cosmetic composition is impregnated.

3. The cosmetic product according to claim 1, wherein the polyether-based urethane foam has an open cell structure before the cosmetic composition is impregnated.

4. The cosmetic product according to claim 1, wherein the emulsified cosmetic composition has a viscosity of 5000-15000 cps.

5. The cosmetic product according to claim 1, wherein the cosmetic composition is make-up primer, make-up base, foundation, powder, twin cake, lipstick, lip gloss, eye shadow, eye brow, concealer or blusher.

6. A cosmetic product consisting essentially of polyether-based urethane foam impregnated with a cosmetic composition which has a reticulated structure wherein the cosmetic composition is discharged from the polyether-based urethane foam to a cosmetic applicator and wherein the cosmetic applicator is detached from the polyether-based urethane foam, wherein the density of the polyether-based urethane foam is 1-3 pcf (pounds per cubic feet) before the cosmetic composition is impregnated, and wherein the polyether-bases urethane foam has a pore number of 70-120 ppi (number of pores per inch) before the cosmetic composition is impregnated.

7. A cosmetic product comprising:
a polyether-based urethane foam impregnated with a cosmetic composition, the polyether-based urethane foam having a reticulated structure;
a container, in which the polyether-based urethane foam impregnated with the cosmetic composition is disposed; and
a cosmetic applicator for applying the cosmetic composition to a skin,
wherein the cosmetic composition is discharged from the polyether-based urethane foam to the cosmetic applicator and wherein the cosmetic applicator is detached from the polyether-based urethane foam,
wherein the density of the polyether-based urethane foam is 1-3 pcf (pounds per cubic feet) before the cosmetic composition is impregnated,
wherein the polyether-based urethane foam has a pore number of 70-120 ppi (number of pores per inch) before the cosmetic composition is impregnated, and
wherein the cosmetic composition is a water in oil (W/O) type or oil in water (O/W) type emulsified cosmetic composition.

8. The cosmetic product according to claim 7, wherein the polyether-based urethane foam has a hardness of 10-70 being measured with a durometer before the cosmetic composition is impregnated.

9. The cosmetic product according to claim 7, wherein the polyether-based urethane foam has an open cell structure before the cosmetic composition is impregnated.

10. The cosmetic product according to claim 7, wherein the emulsified cosmetic composition has a viscosity of 5000-15000 cps.

11. The cosmetic product according to claim 7, wherein the cosmetic composition is make-up primer, make-up base, foundation, powder, twin cake, lipstick, lip gloss, eye shadow, eye brow, concealer or blusher.

12. The cosmetic product according to claim 1, wherein the density of the polyether-based urethane foam is 1-2 pcf (pounds per cubic feet) determined by ASTM D3547 before the cosmetic composition is impregnated.

13. The cosmetic product according to claim 1, wherein the density of the polyether-based urethane foam is 2-3 pcf (pounds per cubic feet) determined by ASTM D3547 before the cosmetic composition is impregnated.

14. The cosmetic product according to claim 7, wherein the density of the polyether-based urethane foam is 1-2 pcf (pounds per cubic feet) determined by ASTM D3547 before the cosmetic composition is impregnated.

15. The cosmetic product according to claim 7, wherein the density of the polyether-based urethane foam is 2-3 pcf (pounds per cubic feet) determined by ASTM D3547 before the cosmetic composition is impregnated.

* * * * *